United States Patent
Tran

(10) Patent No.: US 10,709,568 B2
(45) Date of Patent: Jul. 14, 2020

(54) INTERVERTEBRAL BODY SPACER ASSEMBLY AND KIT

(71) Applicant: Hoan Phan Tran, Naches, WA (US)

(72) Inventor: Hoan Phan Tran, Naches, WA (US)

( * ) Notice: Subject to any disclaimer, the term of this patent is extended or adjusted under 35 U.S.C. 154(b) by 170 days.

(21) Appl. No.: 16/122,006

(22) Filed: Sep. 5, 2018

(65) Prior Publication Data

US 2019/0000635 A1 Jan. 3, 2019

Related U.S. Application Data

(62) Division of application No. 15/159,440, filed on May 19, 2016, now Pat. No. 10,080,665.

(60) Provisional application No. 62/171,933, filed on Jun. 5, 2015.

(51) Int. Cl.
| | | |
|---|---|---|
| *A61F 2/44* | (2006.01) | |
| *A61B 17/16* | (2006.01) | |
| *A61M 29/00* | (2006.01) | |
| *A61B 5/00* | (2006.01) | |
| *A61F 2/46* | (2006.01) | |
| *A61F 2/30* | (2006.01) | |

(52) U.S. Cl.
CPC ............ *A61F 2/442* (2013.01); *A61B 5/4893* (2013.01); *A61B 17/1659* (2013.01); *A61B 17/1671* (2013.01); *A61F 2/4455* (2013.01); *A61F 2/4684* (2013.01); *A61M 29/00* (2013.01); *A61B 5/407* (2013.01); *A61B 5/4896* (2013.01); *A61B 2505/05* (2013.01); *A61F 2002/30471* (2013.01); *A61F 2002/30604* (2013.01); *A61F 2002/4415* (2013.01); *A61F 2002/4677* (2013.01)

(58) Field of Classification Search
CPC .............................. A61F 2/442; A61F 2/4455
See application file for complete search history.

(56) References Cited

U.S. PATENT DOCUMENTS

| | | | | |
|---|---|---|---|---|
| 4,997,432 A | * | 3/1991 | Keller | A61B 17/025 600/219 |
| 5,702,454 A | * | 12/1997 | Baumgartner | A61F 2/4611 128/898 |
| 6,387,130 B1 | * | 5/2002 | Stone | A61F 2/4455 623/17.16 |
| 7,267,690 B2 | * | 9/2007 | Felt | A61F 2/442 623/17.11 |
| 2002/0138146 A1 | * | 9/2002 | Jackson | A61F 2/4455 623/17.15 |
| 2004/0097928 A1 | | 5/2004 | Zdeblick et al. | |
| 2004/0230100 A1 | | 11/2004 | Shluzas | |
| 2010/0076502 A1 | | 3/2010 | Guyer et al. | |

\* cited by examiner

*Primary Examiner* — Christian A Sevilla
(74) *Attorney, Agent, or Firm* — Seed Intellectual Property Law Group LLP

(57) ABSTRACT

An intervertebral spacer assembly having a plurality of articulated intervertebral spacers coupled in series, each intervertebral spacer releasably and connectable to an adjacent intervertebral spacer, each intervertebral spacer having a cannula extending from a first exterior surface of a tail portion through a nose portion to reach a second exterior surface of the nose portion.

11 Claims, 11 Drawing Sheets

INTERVERTEBRAL BODY SPACER ASSEMBLY AND KIT

BACKGROUND

Technical Field

The present disclosure generally relates to various devices and approaches to perform intervertebral discectomy and implant and, more particularly, to a modular intervertebral spacer assembly, a hinged disc shaver assembly, a poly-sensor dilator, and a retroperitoneal retropsoas approach to perform anterior arthrodesis from a traditional prone position.

Description of the Related Art

Spinal disease such as spinal deformity or degeneration is a major cause of disability and pain in the human population, particularly among aging persons and persons who have suffered traumatic spinal injuries. Multiple conditions cause pain by compression of nerve roots. For example, sagittal imbalance, coronal imbalance, rotational imbalance, or other conditions can lead to failure of spinal integrity and associated pain and disability.

When the integrity of the spine fails, a traditional solution would be to perform arthrodesis of the spinal segments. Many spinal implant systems and spinal approaches have been developed to deal with this. One procedure which remains a mainstay for dealing with the failing spine is intervertebral arthrodesis and posterior elements supplementation. For example, the most common spine surgery is lumbar disc surgery in which the subject is most commonly positioned in the prone position.

Intervertebral arthrodesis is typically accomplished by removing the disc between vertebral bodies. Next, an intervertebral spacer is implanted in the vacated disc space. The intervertebral spacer provides structural integrity between the vertebra and allows for arthrodesis, or bony fusion, to occur for long term correction of the spine disease. Supplemental implants may be placed on/in the posterior elements for additional structural support while arthrodesis occurs.

With the introduction of fluoroscopy, microscopy and endoscopy to lumbar spine surgery, the size of incisions has decreased, along with the degree of soft tissue dissection required to approach surgical targets. This is invariably coupled with a decrease in visual field when compared to open surgery, and is a major barrier when transitioning open access surgeons to minimally invasive surgery. The philosophy of minimally invasive surgery (MIS) is maximizing clinical outcomes, while minimizing trauma to surrounding tissue, to achieve the same clinical result as open procedures.

Traditional prone position for spinal fusion allows access to the nerve roots directly but is limited by the small "footprint" that is allowed for arthrodesis. In particular, posterior approaches to the spine for posterior arthrodesis traverse the spinal canal, juxtapose the dura and exiting nerve roots, require retraction of the dura, and only permit implantation of spacers that are quite small compared to the actual disc space.

Common posterior approaches include Posterior Lumbar Intervertebral Fusion (PLIF) and transforaminal lumbar intervertebral fusion (TLIF). These approaches have the advantage of being performed with the subject in the most familiar positioning during surgery: the prone position. However the disadvantage is that such approaches do not allow for placement of larger, more robust implants for arthrodesis.

These disadvantages have led to anterior arthrodesis approaches. One advantage of anterior arthrodesis approaches is the ability to insert an implant with a much larger surface area for arthrodesis relative to posterior approaches. However these anterior methods are limited in the direct decompression of neural elements. In addition, these techniques require the subject to be supine or lateral decubitus position, which is unfamiliar for most spine surgeons, thereby requiring an access surgeon, whom is not always available. Further, if there is a need for posterior element instrumentation, which is often the case, then a second surgery or second position is required to achieve complete surgical intervention.

Common anterior approaches include the anterior lumbar intervertebral fusion and the extreme lateral intervertebral fusion (XLIF). Anterior arthrodesis approaches traditionally require an approach surgeon to reach the retroperitoneal space, prior to preparing the disc space for receiving implant. For example, XLIF requires traversing the retroperitoneal space in the decubitus position, a non-traditional position for spine surgeons. XLIF approaches also require traversing through the psoas muscle, where the lumbar plexus is intimately embedded.

Thus, more creative surgical approaches, such as Axial Lateral intervertebral fusion (AxialLIF) and XLIF, lack the familiarity in positioning or anatomical approaches to gain proficiency quickly and avoid unintended complications. The need for access surgeons for procedures such as ALIF, XLIF, or thorascopy often limit the procedure's ubiquity.

Furthermore, a significant limitation of current retroperitoneal approaches is that they are performed with the subject in the lateral decubitus position, requiring the surgeon to traverse a space that spine surgeons are not traditionally familiar with, and where frequently debated complications may occur. Many of the problems associated with approaches in which the subject is in the lateral decubitus position arise from the proximity of the vital structures such as the ureters, aorta, inferior vena cava, etc., in the surgical field.

Direct lateral transpsoas approaches have been described since the early 2000's for intervertebral fusion, including the XLIF and direct lateral fusion (DLIF) approaches. However, significant controversy about the safety of direct lateral transpsoas approach remains, despite industry efforts for surgeon education.

BRIEF SUMMARY

The present disclosure provides a surgical method and devices for accessing intervertebral disc space, performing disc removal, and deploying intervertebral spacers for the purpose of anterior arthrodesis of a subject.

In particular, the present disclosure is directed to devices and methods which permit a surgeon to access the intervertebral disc space through a safe retroperitoneal, retropsoas approach and perform spinal discectomy and implant on a subject in the traditional prone position. The present disclosure is also directed to implantable modular interlocking intervertebral spacers for subject-specific spinal stabilization, deformity correction, and improved arthrodesis.

The presently provided approach enables access to the target disc space through Kambin's triangle, which is an anatomical safe zone, and circumvents the exiting nerve root and its accompanying radicular artery. This procedure is also performed in the prone position, a position that all spine surgeons are comfortable with.

According to an aspect of the present disclosure, the subject is placed prone on a radiolucent operating table. The contents of the abdomen and the retroperitoneal space therefore fall forward with gravity. After sterile preparation of the surgical site, a transverse incision is made in the posterolateral flank, approximately 8-12 centimeters from the midline, depending on the side of the targeted disc, parallel to the targeted disc space. Once the incision is made, sharp dissection is made deeply to the lateral edge of the quadratus lumborum or external oblique muscles. Blunt dissection is made into the retroperitoneal space through the transversalis fascia using a closed Mayo scissors or hemostat. Blunt digital dissection is made towards the midline in the retroperioteal space towards the transverse process. Once the tip of the transverse process is palpated, digital dissection/Kittner dissection is carried on the ventral side of the transverse process, down the lateral aspect of the pedicle and to the root of the pedicle. Next, dissection is performed cranially towards the targeted disc space.

The above-described method of accessing the disc space is unique in that it permits access to the "anterior" portion of the vertebral column from a prone subject position.

Next, the surgical cavity is created with blunt dissection from the skin to the targeted disc. A blunt dilator is placed posterolaterally on the disc space, abutting against the adjacent facet joint. Once the blunt dilator is in place, a direct neurostimulator is placed in a cannulated portion of the dilator or other inserted device, to make sure there is no traversing nerves under the dissector or dilator. Minor adjustments are made to avoid the exiting nerve. Additional dilators may be made over the disc space if required. Long surgical retractors are placed over the dilators on the targeted disc, in preparation for discectomy.

The present disclosure also provides unique instruments that allow for disc removal and other surgical tasks. A hinged disc shaver assembly is described which includes two or more hinged, paddle-shaped disc shavers. The hinged disc shavers assembly is such that the shavers are segmented and permitted to pivot or turn around certain angles. In some implementations, certain hinges of the instruments can be tightened to maintain its shape.

The hinged disc shaver assembly is placed down the retractor, advanced across the disc space, and then rotated along its long axis to disrupt the disc. The disruptive procedure can be repeated with different size disc shavers or shaver assemblies.

A novel multidirectional pituitary rongeur is also described. The pituitary rongeur is placed down the retractor and into the disc space to remove disc fragments. Novel multidirectional curettes are also described. The multidirectional curettes are passed down the retractor and employed to rasp the vertebral endplates for arthrodesis. Next, trial intervertebral spacers are placed into the disc space to size for permanent intervertebral spacer implants.

More particularly, the present disclosure provides various novel designs and structures for both trial and permanent intervertebral spacers. As an example, the present disclosure provides modular intervertebral spacers which are sized and shaped to nest or complementarily fit, mate, or interlock with each other. The modular intervertebral spacers may have varying or asymmetric dimensions in one or more of the sagittal, coronal, or transverse planes.

Such varying or asymmetric dimensions enable selection of particular modular intervertebral spacers based on a particular subject's pathology. For example, intervertebral spacers having varying or asymmetric dimensions in one or more of the sagittal, coronal, or transverse planes can be selected and assembled to correct or otherwise accommodate a particular subject pathology which presents a coronal, sagittal, or rotational deformity.

Thus, segmental, modular, interlocking intervertebral spacers are chosen for the targeted disc space depending upon the particular subject pathology. The selected intervertebral spacers are then assembled on a multidirectional coaxial implant inserter. The respective angles of the intervertebral spacers are set with the implant inserter. The spacer assembly and inserter is passed into the disc space.

The devices and methods of the present disclosure allow for individualized number of intervertebral spacers, one or more, chosen for individual discs pathology. The length, width and height can be chosen of the segmental spacers to correct for coronal or sagittal deformity correction.

One aspect of the present disclosure is directed to an intervertebral spacer kit which may be summarized as including a plurality of candidate intervertebral spacers. Each of the plurality of candidate intervertebral spacers may be releasably connectable to at least one other of the plurality of candidate intervertebral spacers. At least one of the plurality of candidate intervertebral spacers has different dimensions than others of the plurality of candidate intervertebral spacers.

The plurality of candidate intervertebral spacers may include a plurality of modular candidate intervertebral spacers. Each modular candidate intervertebral spacer may have a first end and a second end. The first end may be sized and shaped to nest with the second end of an adjacent modular candidate intervertebral spacer to form an articulable joint.

At least one of the plurality of candidate intervertebral spacers may have asymmetric coronal dimensions. At least one of the plurality of candidate intervertebral spacers may have asymmetric sagittal dimensions.

Another aspect of the present disclosure is directed to an intervertebral spacer assembly which may be summarized as including: a plurality of articulated intervertebral spacers coupled in series. Each intervertebral spacer may be releasably connectable to an adjacent intervertebral spacer.

The plurality of intervertebral spacers may be selected from a plurality of candidate intervertebral spacers. At least one of the plurality of candidate intervertebral spacers may have different dimensions than remaining candidate intervertebral spacers.

Each intervertebral spacer of the plurality of intervertebral spacers may have a respective cannula extending through the intervertebral spacer. The cannula of each intervertebral spacer may be sized and shaped to receive a wire inserted therethrough.

The intervertebral spacer assembly may further include: the wire extending through the cannula of each of the plurality of intervertebral spacers.

Each intervertebral spacer may have a first end having a nose portion and an opposing second end having a tail portion. The nose portion may be sized and shaped to complementarily fit into the tail portion of an adjacent intervertebral spacer. The nose portion may have a rounded bullet-shape and the tail portion may have a concave shape sized and shaped to receive the nose portion of at least one other intervertebral spacer of the plurality of intervertebral spacers. Each intervertebral spacer may have a cannula extending from a first exterior surface of the tail portion through the nose portion to reach a second exterior surface of the nose portion.

The plurality of intervertebral spacers may include a leading spacer, a middle spacer, and a trailing spacer. The leading spacer may be articulatably coupled to the middle spacer and the middle spacer may be articulatably coupled to the trailing spacer. The leading spacer may have a first end and a second end opposite the first end; the middle spacer may have a third end and a fourth end opposite the third end; and the trailing spacer may have a fifth end and a sixth end opposite the fifth end. The second end and the third end may respectively have a first pair of complementary mating structures and the fourth end and the fifth end may respectively have a second pair of complementary mating structures.

Another aspect of the present disclosure is directed to a dilator which may be summarized as including: a non-conductive body that is elongated along a longitudinal axis and that includes a plurality of cannulas that extend parallel to the longitudinal axis at a plurality of different cross-sectional positions of the body; and a plurality of conductive elements that respectively extend through the plurality of cannulas to an outer surface of a first end of the body. The body may include three concentric body elements that respectively have three different lengths along the longitudinal axis.

Another aspect of the present disclosure is directed to a disc shaver assembly which may be summarized as including: a plurality of shavers coupled in series. Each of the plurality of shavers may be hingedly coupled to at least one other of the plurality of shavers. The disc shaver assembly further includes a handle coupled to a first shaver of the plurality of shavers. Each of the plurality of shavers may be paddle-shaped.

The first shaver may have a ball protruding from a first end of the first shaver. The handle may have a socket at a second end of the handle. The socket may be sized and shaped to complementarily receive the ball. One or both of the ball and socket may have one or more structures which transmit rotational force from the socket to the ball.

Another aspect of the present disclosure is directed to a method of performing surgery on a spine of a subject positioned in a prone position which may be summarized as including: making an incision in a posterolateral flank of the subject; performing dissection from the incision at least toward a quadratus lumborum muscle or an external oblique muscle of the subject; performing dissection into the retroperitoneal space through the transversalis fascia; and accessing a target disc space in the spine via the retroperitoneal space.

Making an incision in a posterolateral flank of the subject may include making a transverse incision in the posterolateral flank of the subject parallel to the target disc space.

Performing dissection from the incision at least toward a quadratus lumborum muscle or an external oblique muscle of the subject may include performing dissection anteriorly from the incision to at least achieve a retropsoas position without incising a psoas muscle of the subject.

Performing dissection from the incision at least toward a quadratus lumborum muscle or an external oblique muscle of the subject may include performing sharp dissection to a lateral edge of the quadratus lumborum muscle or the external oblique muscle of the subject.

Accessing a target disc space in the spine via the retroperitoneal space may include: performing dissection through the retroperitoneal space toward the midline to reach a transverse process of a lower target vertebra; performing dissection from the transverse process of the lower target vertebra along a lateral aspect of a pedicle of the lower target vertebra to reach a root of the pedicle of the lower target vertebra; and performing dissection cranially from the root of the pedicle of the lower target vertebra to expose the target disc space.

The method may further include: selecting two or more first trial intervertebral spacers from a plurality of trial intervertebral spacers. At least one of the plurality of trial intervertebral spacers may have different dimensions than others of the plurality of trial intervertebral spacers. The method may further include: inserting the two or more first trial intervertebral spacers into the target disc space to determine a fit of the selected two or more first trial intervertebral spacers within the target disc space.

The method may further include: selecting two or more first permanent intervertebral spacers from a plurality of permanent intervertebral spacers based at least in part on the fit of the selected two or more first trial intervertebral spacers within the target disc space. At least some of the plurality of permanent intervertebral spacers have different dimensions that at least others of the plurality of permanent intervertebral spacers. The method may further include: inserting the two or more first permanent intervertebral spacers into the target disc space.

The method may further include: prior to inserting the two or more first permanent intervertebral spacers into the target disc space, inserting a wire through two or more cannulas extending through the two or more first permanent intervertebral spacers to assemble the two or more first permanent intervertebral spacers into an intervertebral spacer assembly. The method may further include: after inserting the two or more first permanent intervertebral spacers into the target disc space, removing the wire from the two or more cannulas respectively extending through the two or more first permanent intervertebral spacers.

BRIEF DESCRIPTION OF THE SEVERAL VIEWS OF THE DRAWINGS

The foregoing and other features and advantages of the present disclosure will be more readily appreciated as the same become better understood from the following detailed description when taken in conjunction with the accompanying drawings, wherein.

DETAILED DESCRIPTION

Figure 1A:
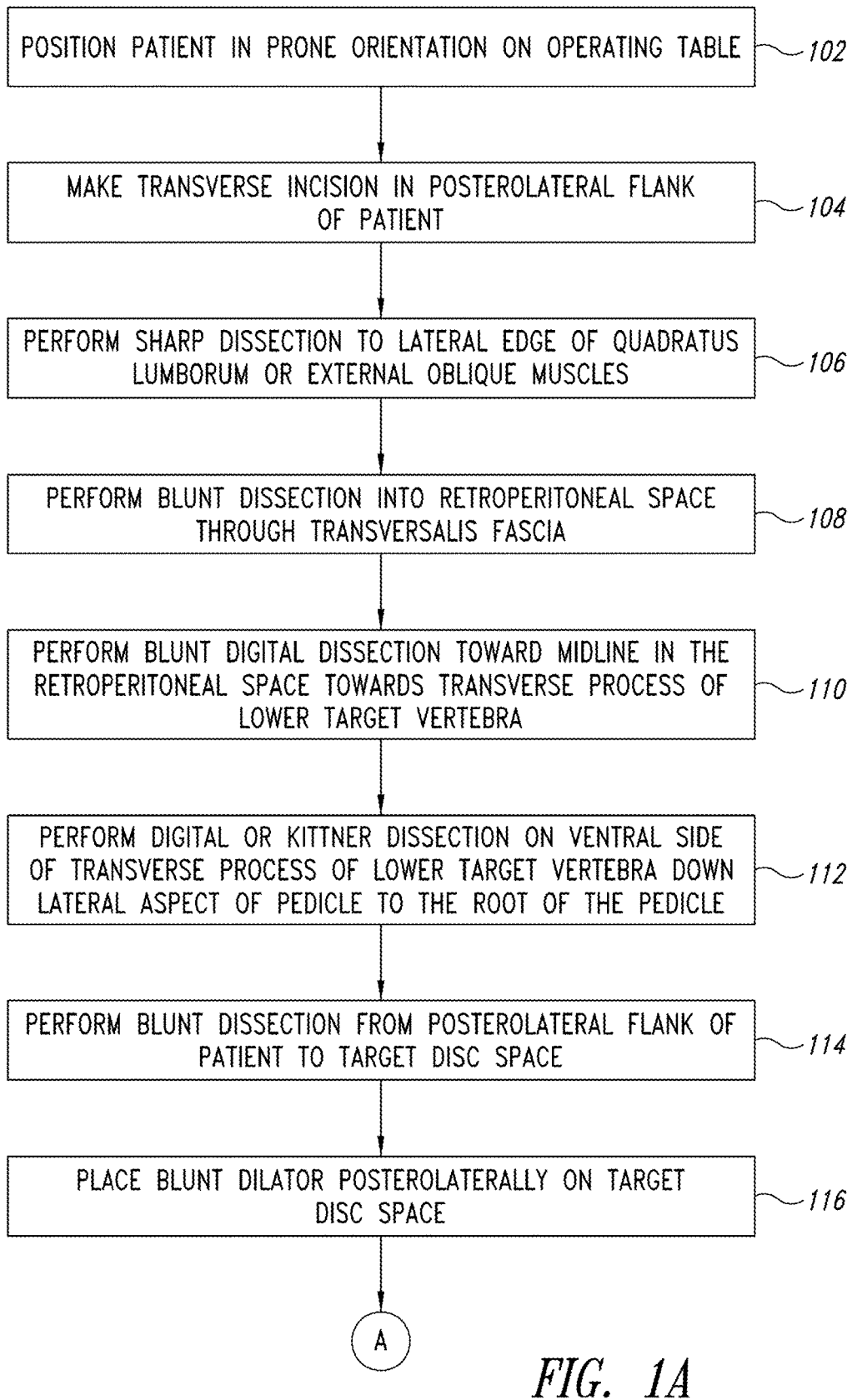
FIGS. 1A-1C are a flow chart diagram of an example method to perform intervertebral discectomy and implant, according to an example implementation of the present disclosure.

In the following description, certain specific details are set forth in order to provide a thorough understanding of various disclosed implementations. However, one skilled in the relevant art will recognize that implementations may be practiced without one or more of these specific details, or with other methods, components, materials, etc. In other instances, well-known structures have not been shown or described in detail to avoid unnecessarily obscuring descriptions of the implementations.

Unless the context requires otherwise, throughout the specification and claims that follow, the word "comprising" is synonymous with "including," and is inclusive or open-ended (i.e., does not exclude additional, unrecited elements or method acts).

Reference throughout this specification to "one implementation" or "an implementation" means that a particular feature, structure or characteristic described in connection with the implementation is included in at least one implementation. Thus, the appearances of the phrases "in one implementation" or "in an implementation" in various places throughout this specification are not necessarily all referring to the same implementation. Furthermore, the particular features, structures, or characteristics may be combined in any suitable manner in one or more implementations.

As used in this specification and the appended claims, the singular forms "a," "an," and "the" include plural referents unless the context clearly dictates otherwise.

As used in herein, the terms "subject" and "patient" include any member of the animal kingdom which is the subject of a surgery, and includes humans, dogs, cats, horses, or other mammals. "Articulatable" means capable of relative movement in either one plane, two planes, or three planes. This can include a hinged connection, a ball joint connection, and multiple hinged or ball joint connections and their functional equivalents as well-known in the art.

The headings and Abstract of the Disclosure provided herein are for convenience only and do not interpret the scope or meaning of the implementations.

In the drawings, identical reference numbers identify similar elements or acts. The sizes and relative positions of elements in the drawings are not necessarily drawn to scale. For example, the shapes of various elements and angles are not necessarily drawn to scale, and some of these elements may be enlarged and positioned to improve drawing legibility.

The present invention describes an approach for accessing a target disc space, instruments for preparing the disc space, and modular interlocking intervertebral spacers that allow for spine stabilization, structural integrity for arthrodesis, individualized correction of spinal deformity, and direct and indirect decompression of neural elements.

Figure 1B:
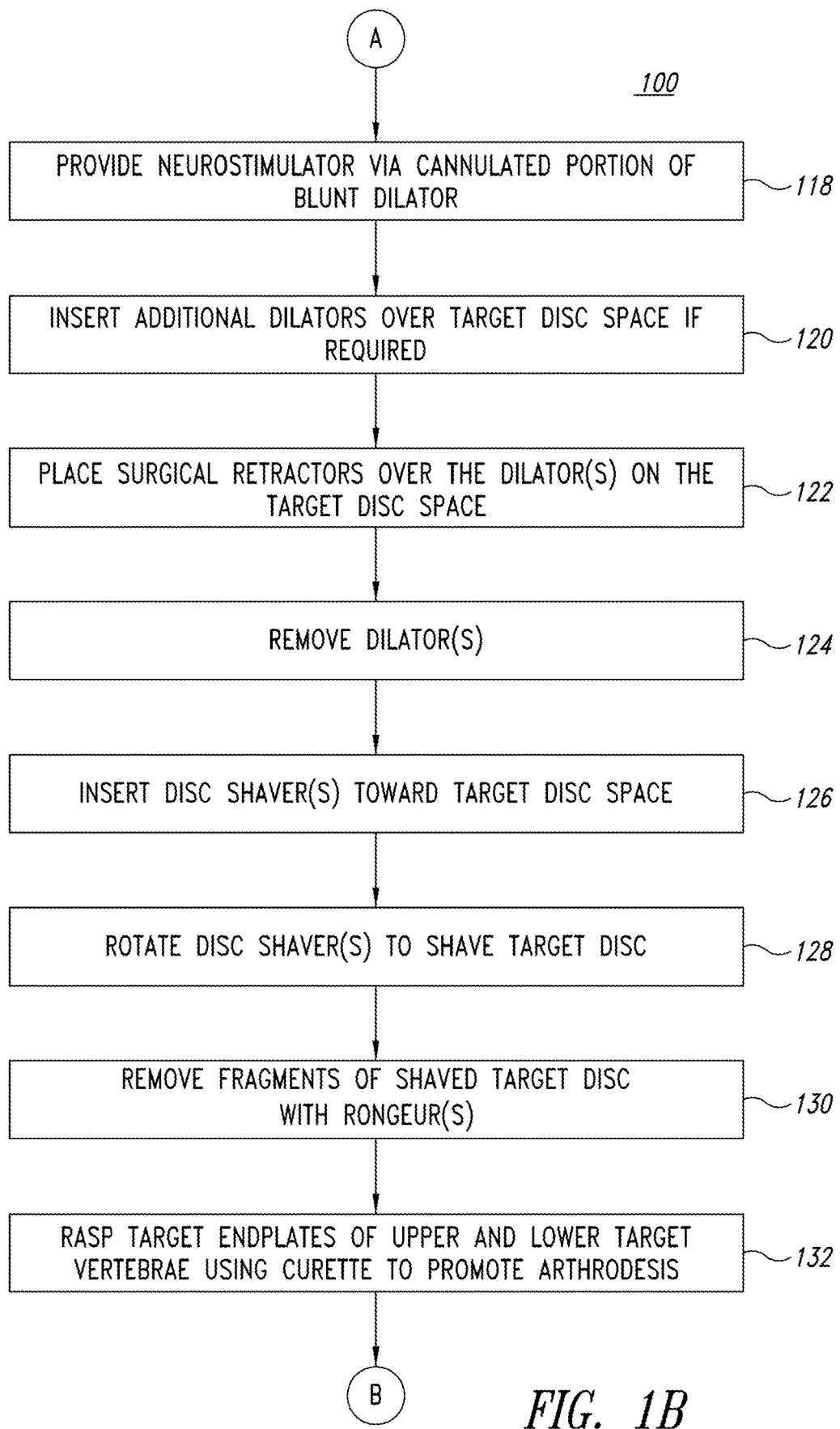
Figure 1C:
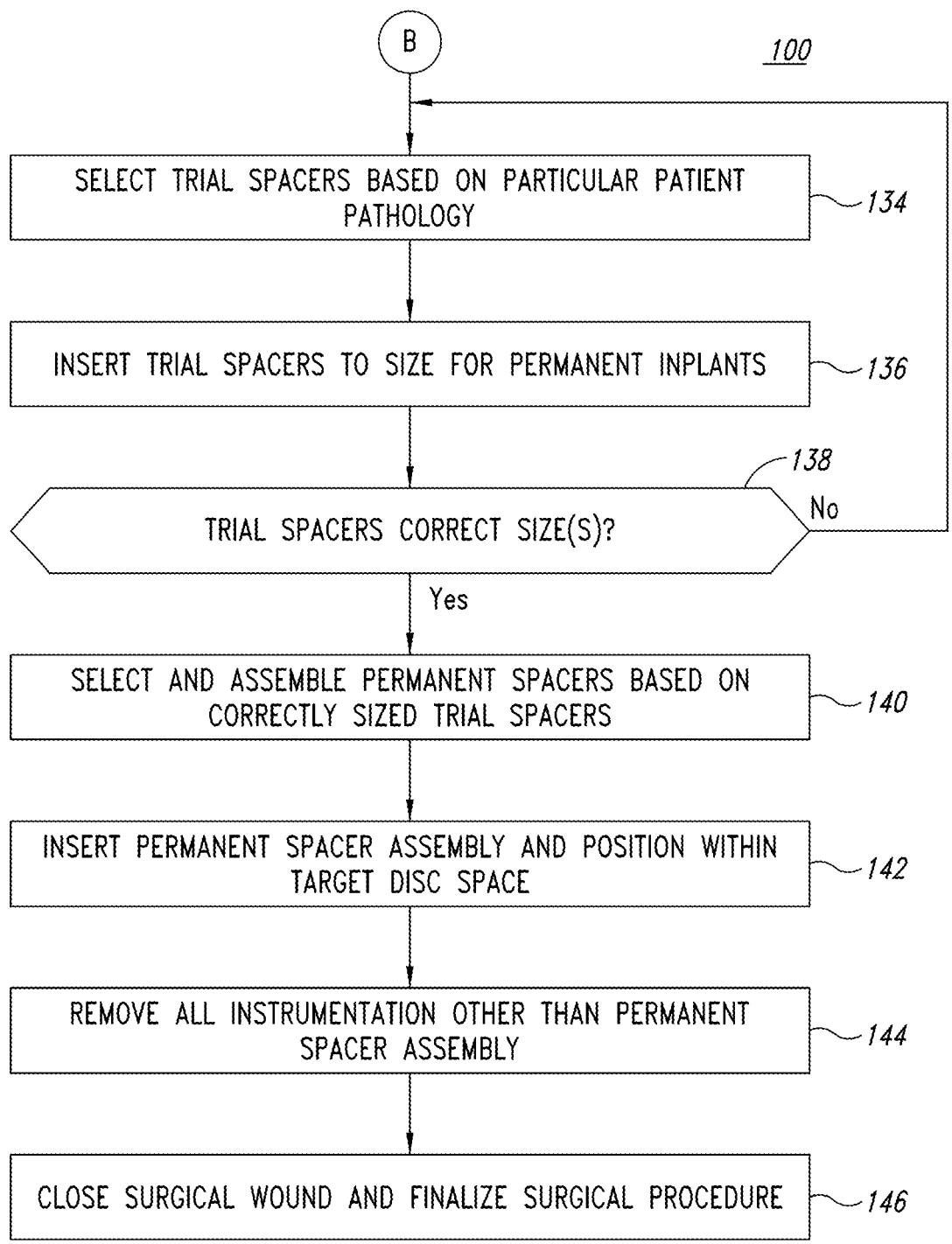

FIGS. 1A-1C are a flow chart diagram of an example method 100 to perform intervertebral discectomy and implant, according to an example implementation of the present disclosure.

Referring first to FIG. 1A, the method 100 begins at 102. At 102, the subject is placed in a prone position on an open radiolucent operating table. This allows the abdominal contents to fall forward. Neuromonitoring electrodes are placed on the lower extremities to monitor end muscles of the lumbar plexus. Fluoroscopy is brought into the surgical field and pedicles and end plates of the targeted levels are projected on the flank of the subject. Thus, method 100 employs a prone oblique approach, which allows for familiarity of the prone approach to the spine. However, contrary to existing prone approaches, method 100 permits implantation of intervertebral spacers through an anterior arthrodesis approach that allows for a large footprint for arthrodesis.

At 104, the surgeon makes a transverse incision in a posterolateral flank of the subject. For example, the surgeon makes a 2 cm incision transversely in line with targeted disc, approximately 16-18 cm from the midline. Such location of incision is just over the lateral edge of the quadratus lumborum, which is usually mid-iliac crest line on an AP projection of the fluoroscopy.

At 106, the surgeon performs sharp dissection to the lateral edge of the quadratus lumborum muscle or external oblique muscles of the subject. For example, dissection is carried from the skin to the deep fascia. The deep fascia incision is parallel to the skin incision.

At 108, the surgeon performs blunt dissection through the transversalis fascia into the retroperitoneal space of the subject. For example, the quadratus lumborum is entered bluntly with finger dissection or closed curved mayo to an anterior sheath of the quadratus lumborum, through the transversalis fascia into the retroperitoneal space.

At 110, the surgeon performs digital dissection toward a midline of the subject in the retroperitoneal space towards a transverse process of a lower target vertebra. Digital dissection of the retroperitoneal space pushes retroperitoneal contents forward. Gravity from being prone on an open radiolucent spine table also allows abdominal contents to migrate forward.

Thus, at 110 digital dissection is performed along the anterior surface of the quadratus lumborum fascia, and medial towards the transverse processes in a side-to-side sweeping motion.

At 112, the surgeon performs digital or Kittner dissection on a ventral side of the transverse process of the lower target vertebra down the lateral aspect of the pedicle to the root of the pedicle. For example, once the tip of the transverse process is palpated, a small blunt dissector is placed at the ventral tip of the transverse process, and advanced medially towards the pedicle. The dissector is now placed in the retropsoas space. The blunt dissector is moved forward to the root of the pedicle, "walking down the pedicle", and just cranial to the root of the pedicle is the disc space. The blunt dissector is advanced cranially to the disc space into Kambin's triangle. The dissector also has a neuromonitoring probe that can detect and map nerves in proximity of the surgical field.

At 114, the surgeon performs blunt dissection from the posterolateral flank of the subject to the target disc space. For example, once fluoroscopy and neuromonitoring confirm that the probe and dissector is not compressing the exiting nerve, one or more sequential dilators are placed over the initial blunt dissector, to push the psoas muscle and all the contents forward. Fluoroscopy can be used to confirm the placement of the probe and dilators.

Thus, at 116, the surgeon places a blunt dilator posterolaterally onto the target disc space. Referring now to FIG. 1B, at 118, the surgeon provides a neurostimulator via a cannulated portion of the blunt dilator to detect and map nerves in proximity of the surgical field. At 120, the surgeon inserts additional dilators over the target disc space if required.

Figure 2:
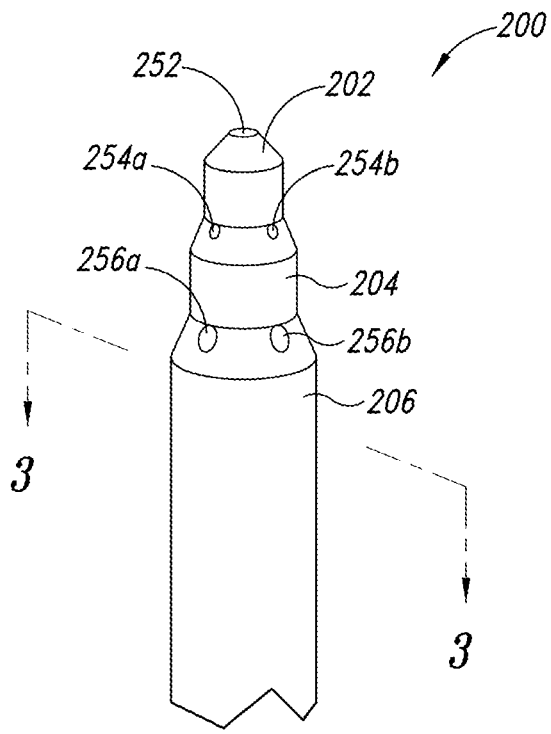
FIG. 2 is a perspective view of an example poly-sensor dilator, according to an example implementation of the present disclosure.
Figure 3:
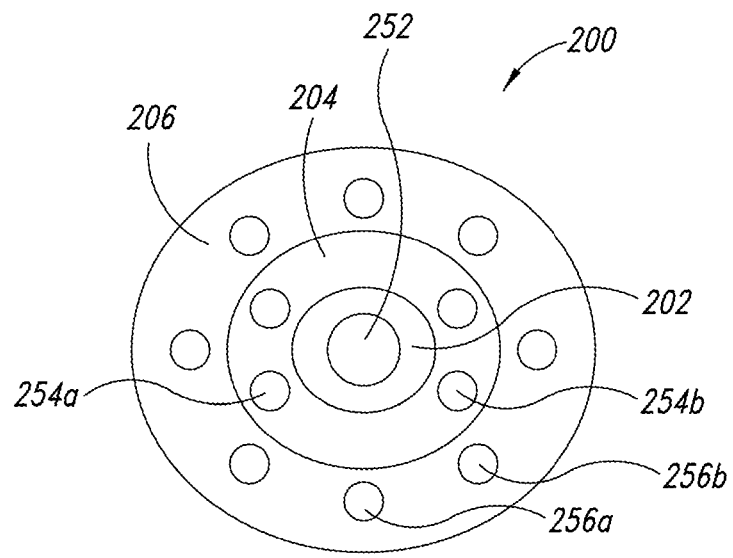
FIG. 3 is a cross sectional view of the poly-sensor dilator of FIG. 2, according to an example implementation of the present disclosure.

To provide one example of a dilator which may be used, FIG. 2 is a perspective view of a poly-sensor dilator 200, according to an example implementation of the present disclosure. FIG. 3 is a cross sectional view of the poly-sensor dilator 200 of FIG. 2.

The dilator 200 includes a body that is elongated along a longitudinal axis. The body includes a plurality of cannulas that extend parallel to the longitudinal axis at a plurality of different cross-sectional positions of the body.

The body includes three concentric dilator body elements 202, 204, and 206 which complementarily fit over each other. Each body element may be insertable around the next sequential body element. The dilator body elements 202, 204, and 206 respectively have three different lengths along the longitudinal axis. As shown in FIG. 2, each of the body elements 202, 204, and 206 has a rounded or conical shape at the first end of the dilator 200. As shown in FIG. 3, each of the body elements 202, 204, and 206 has an oval cross sectional shape.

The dilator also includes a plurality of conductive elements (e.g., conductive elements 252, 254a, 254b, 256a, and 256b) that respectively extend through the plurality of cannulas to an outer surface of a first end of the body. For example, as shown in FIGS. 2 and 3, the conductive element 252 extends through the length of the body element 202; the conductive elements 254a and 254b extend through the length of the body element 204; and the conductive elements 256a and 256b extend through the length of the body element 206.

Thus, in contrast to presently available dilators, which include only a single conductive element or sensor assembly, the dilator 200 includes a plurality of different conductive elements, which may each serve as a sensor to detect and map nerve tissue within a surgical area within a subject.

As one example method of operation, once the dilator 200 has been inserted into the surgical would, a variable current can be manually or automatically provided on a particular conductive element of the dilator 200. For example, the current can be ramped from 1 mA to 30 mA. If effects of neurostimulation (e.g., muscle twitch) are detected (e.g., by neuromonitoring electrodes placed on the lower extremities) then an operator or central console of the dilator can determine that nerve tissue is located relatively adjacent to the conductive element on which the current was provided.

The amplitude of the current at which the effects of neurostimulation are detected provides information regarding the relative distance of the nerve tissue from the conductive element. As examples, if effects of neurostimulation are seen at 1 mA, then it can be determined that the nerve tissue is relatively close to the conductive element; if effects of neurostimulation are seen at 30 mA then it can be determined that the nerve tissue is relatively farther away from the conductive element.

The above described procedure can be repeated manually or automatically for each of the conductive elements in a sequential fashion. Thus, by sequentially providing current on the plurality of different conductive elements, a map of nerves in proximity to the surgical field can be created. In particular, because the dilator 200 includes a plurality of conductive elements located at different cross sectional positions, the map can be created without requiring the dilator 200 to be rotated or otherwise manipulated within the wound, as is required for dilators with a single conductive element.

Although the dilator 200 is described with respect to a spinal procedure, dilator 200 is not limited to such procedure and is useful to map nerve tissue in a surgical wound of any kind for any procedure.

Referring again to FIG. 1B, after the surgical opening has been suitably dilated and the absence of nerves directly proximate to the target disc space has been confirmed, then at 122, the surgeon places surgical retractors over the dilator(s) on the target disc space. At 124, the surgeon removes the dilators.

Figure 4:
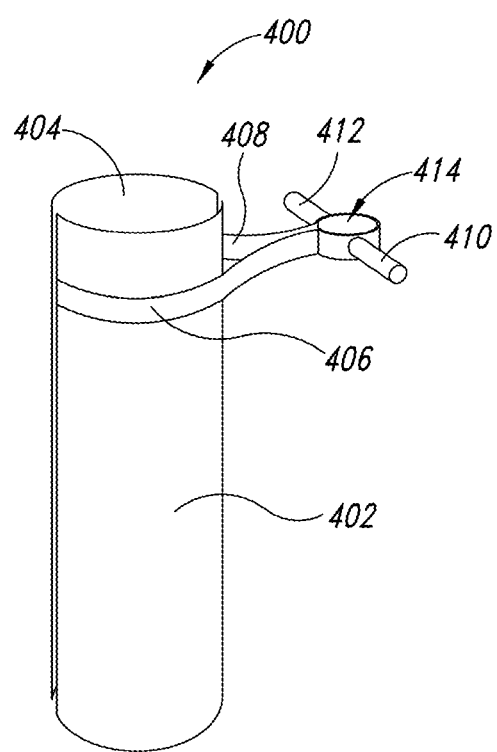
FIG. 4 is a perspective view of an example retractor device, according to an example implementation of the present disclosure.

To provide one example of a surgical retractor which may be used, FIG. 4 is a perspective view of an example retractor device 400, according to an example implementation of the present disclosure.

The retractor 400 has retraction portions which are cumulatively oval in cross section. In particular, the retractor 400 is made of two blades 402 and 404. In some implementations, the retractor 400 has more than two blades. The blades 402 and 404 are each semi-oval in cross section. When in the non-retracting position, the blades 402 and 404 define an elongated oval.

The blades 402 and 404 are respectively held by or otherwise physically coupled to respective arms 406 and 408. The arms 406 and 408 may be mechanically coupled to the respective handle portions 410 and 412 via a pivot mechanism 414. In some implementations, the pivot mechanism includes locking ratchet functionality, which serves to hold the blades 402 and 404 in the retracted position until manually released. In some implementations, as illustrated, the handle portions 410 and 412 respectively extend at 90 degree angles from the portions of arms 406 and 408 to which they are respectively mechanically connected.

To employ the retractor 400 in the presently described spinal procedure, the surgeon places the surgical retractor 400 over the dilator(s) on the target disc space. The retractor is oriented parallel to the disc space and opened so that the blades move cranially and caudally. Once the retractor is in adequate position, the retractor is attached to a holding arm.

Neuroendoscopy or microscopy is used within the retractor to confirm placement of the retractor on the posterolateral annulus, and there are no intersecting nerve roots. A 15-blade or other cutter is used to incise the posterolateral annulus.

Although the retractor 400 is described with respect to a spinal procedure, the retractor 400 is not limited to such procedure and is useful to retract a surgical wound of any kind for any procedure.

Referring again to FIG. 1B, at 126 the surgeon inserts one or more disc shaver(s) in the wound and toward the target disc space. At 128, the surgeon rotations the disc shaver(s) to shave or otherwise disrupt the target disc.

Figures 5, 6:
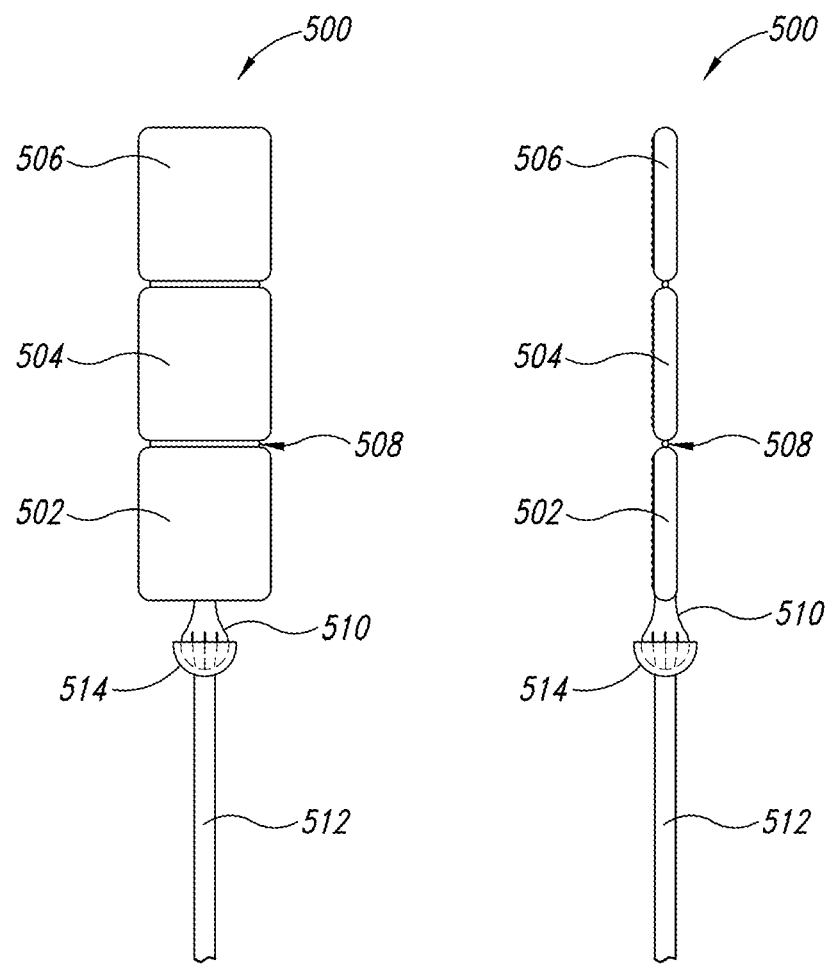
FIG. 5 is a front view of an example hinged disc shaver assembly, according to an example implementation of the present disclosure.
FIG. 6 is a side view of the hinged disc shaver assembly of FIG. 5, according to an example implementation of the present disclosure.

To provide one example of a disc shaver which may be used, FIG. 5 is a front view of an example hinged disc shaver assembly 500, according to an example implementation of the present disclosure. FIG. 6 is a side view of the hinged disc shaver assembly 500 of FIG. 5.

The disc shaver assembly 500 includes a plurality of shavers 502, 504, and 506 coupled in series. In other implementations, the assembly 500 includes two or more shavers coupled in series. Each of the plurality of shavers may be paddle-shaped, as illustrated.

Each of the plurality of shavers 502, 504, and 506 may be hingedly coupled to at least one other of the plurality of shavers. For example, the shaver 502 is hingedly coupled to the shaver 504 by a hinge 508.

The disc shavers 502-506 may have different lengths or widths and may have one or more articulations. The disc shaver assembly 500 is rotated to disrupt the disc. Preparation of the disc space can be performed with conventional disc prep instruments such as angled curettes and suctions.

The disc shaver assembly 500 further includes a handle 512 coupled to the first shaver 502 of the plurality of shavers 502-506. The first shaver 502 may have a ball 510 protruding from a first end of the first shaver 502. The handle 512 may have a socket 514 at a second end of the handle. The socket 514 may be sized and shaped to complementarily receive the ball 512. One or both of the ball 512 and socket 514 may have one or more structures which transmit rotational force from the socket 514 to the ball 512. For example, one or both of the ball 512 and the socket 514 may have one or more grooves or other complementary mating structures which allow some articulation of the ball and socket joint but still effect transfer of rotational force.

According to another aspect, each of the handles 512 and the shavers 502-506 can have a cannula extending therethrough parallel to the longitudinal axis of the shaver assembly 500. A wire can be passed down the cannulated portion of the shavers, bent to hold a specific angle prior to passing the assembly 500 into the disc space, and then removed prior to using (e.g., rotating) the shaver assembly 500. Such may allow the assembly 500 to be shaped prior to insertion into a configuration which more readily permits insertion of the assembly 500 to reach the target disc space. For example, the assembly 500 can be shaped to slide around "sharp corners" during insertion.

One or more surfaces of one or more of the shavers 502-506 may be textured or otherwise have features which aid in disruption of the disc. For example, in one implementation, long hollow tubular cannulated shavers have the ability to be compressed and conform to the disc space. They are hollowed and have a rough "cheese grater" outer surface. The shavers have the inner tube or cannula that accommodates the guide wire. The outer roughed surface have pores in them to allow for disc materials to pass into the cannulated portion of the shaver. The outer pores may be louvered.

In another embodiment, the tubular disc shaver is made out of metal with slots to allow it to bend from straight to 90 degrees. These tubular disc shavers have variably sized "cheese grater" pores on them to allow for large disc fragment removal and fine disc fragment removal.

Referring again to FIG. 1B, at 130, the surgeon removes fragments of the shaver target disc with one or more pituitary rongeur(s). At 132, the surgeon uses a curette to rasp the target endplates of the upper and lower target vertebrae to promote arthrodesis.

Referring now to FIG. 1C, at 134 the surgeon selects one or more trial spacers based on a particular pathology presented by the subject. Thus, once the discectomy is completed, trial spacers are selected. The trial spacers may be sized differently in length, width, or height, and are made of radiopaque materials such as stainless steel. The trial spacers are made to mimic the size of actual or "permanent" spacers that will be permanently implanted into the disc space. The trial spaces will also be cannulated along the length of the trial spacers so that the trial spacers may be passed down a guide wire. Typically, the trial spacers and the permanent spacers will be identical in size and shape, but the trial spacers will be made of less expensive materials.

Figures 7, 8, 9:
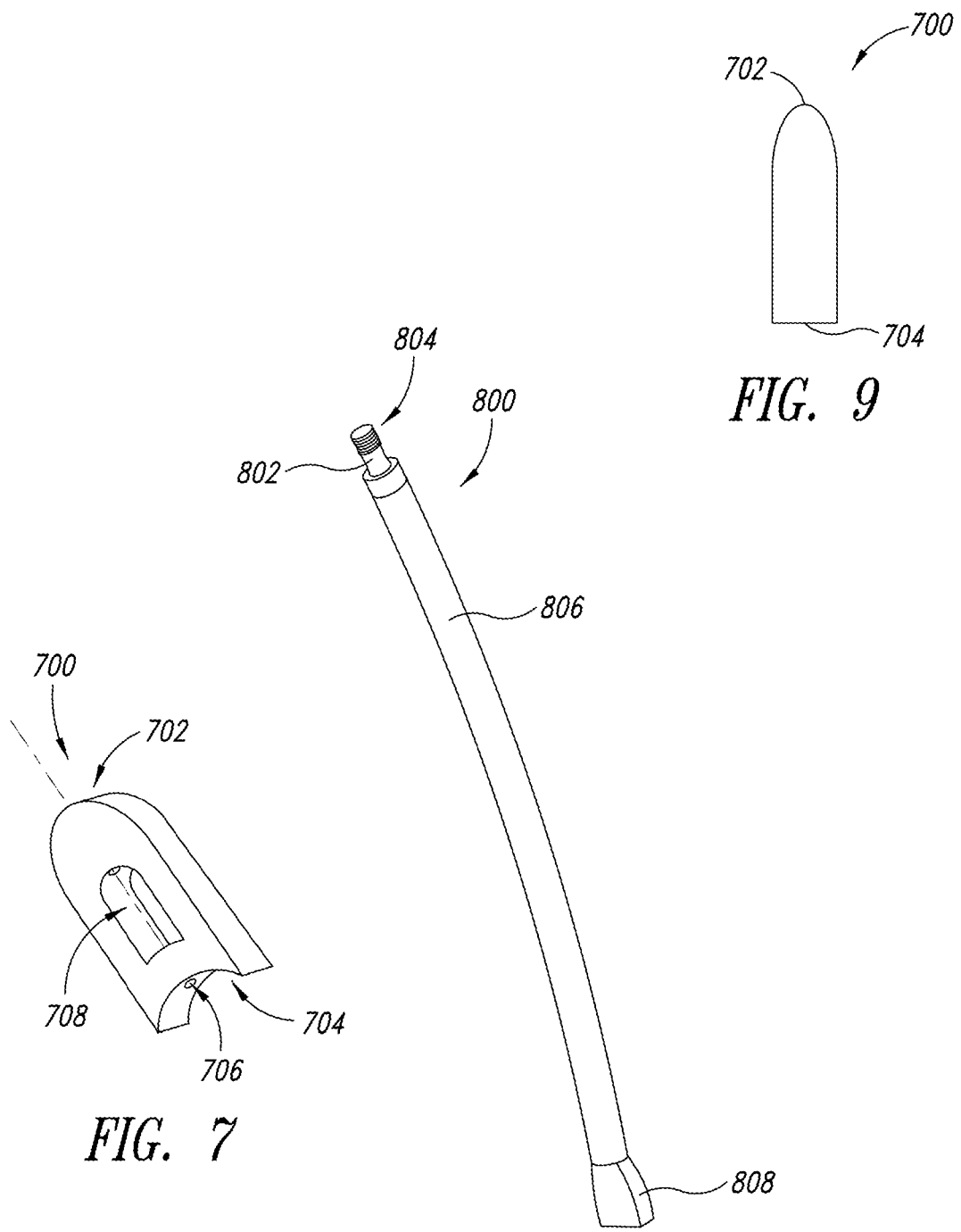
FIG. 7 is an isometric view of an example intervertebral spacer, according to an example implementation of the present disclosure.
FIG. 8 is an isometric view of an example guide wire, according to an example implementation of the present disclosure.
FIG. 9 is a side view of the intervertebral spacer of FIG. 7, according to an example implementation of the present disclosure.

As one example of trial or permanent spacer structure, FIG. 7 is an isometric view of an example intervertebral spacer, according to an example implementation of the present disclosure. FIG. 9 is a side view of the intervertebral spacer of FIG. 7, according to an example implementation of the present disclosure.

The spacer 700 has a first end 702 that has a nose portion and a second end 704 that has a concave tail portion. The nose portion has a rounded bullet shape. A cannula 706 extends through a longitudinal length of the spacer 700. The spacer 700 also has an opening 708 which may hold various substances such as calcium triphosphate, bone marrow, or other injectable substances which improve the arthrodesis. One or more exterior surfaces of the spacer 700 may be textured. For example, one or more exterior surfaces may have teeth which serve to engage or "dig into" an endplate of the abutting vertebra.

FIG. 8 is an isometric view of an example guide wire 800, according to an example implementation of the present disclosure. The guide wire 800 includes an interior wire 802 that has a threaded portion 804 at a first end. The interior wire 802 is coaxially surrounded by a sheath 806. The interior wire 802 may be coaxially slidable relative to the sheath 806. The guide wire 800 includes a tab 808. The tab 808 may allow the interior wire 802 to be actuated relative to the sheath 806 similar to a Bowden cable. Actuation of the interior wire 802 may serve to cinch or otherwise tighten together any spacers located on the guide wire 800. In some implementations, the interior wire 802 can include a bulge or protrusion between the threaded portion 804 and the beginning of the sheath 806.

Figure 10:
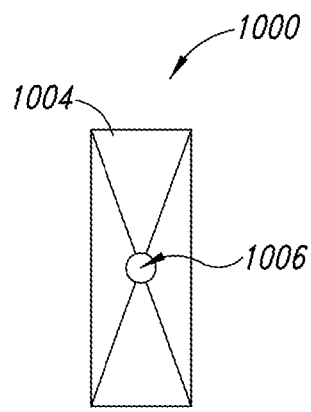
FIG. 10 is a bottom view of an example intervertebral spacer, according to an example implementation of the present disclosure.
Figure 11:
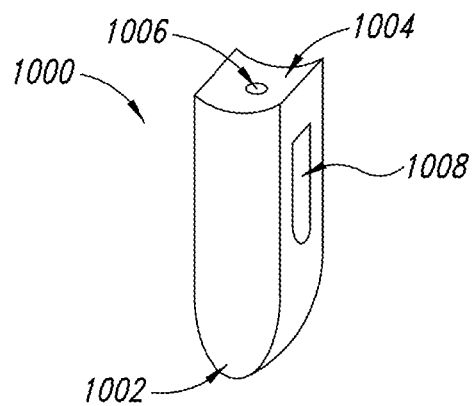
FIG. 11 is an isometric view of the intervertebral spacer of FIG. 10, according to an example implementation of the present disclosure.
Figure 12:
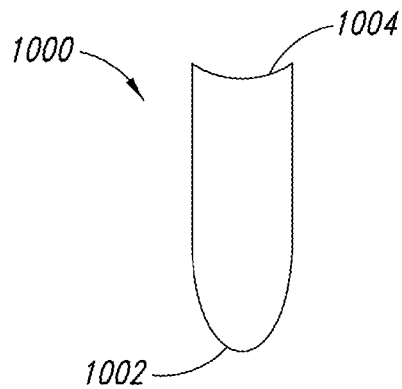
FIG. 12 is a side view of the intervertebral spacer of FIG. 10, according to an example implementation of the present disclosure.

As another example spacer structure, FIG. 10 is a bottom view of an example intervertebral spacer 1000, according to an example implementation of the present disclosure. FIG. 11 is an isometric view of the intervertebral spacer 1000. FIG. 12 is a side view of the intervertebral spacer 1000.

The spacer 1000 has a first end 1002 that has a nose portion and a second end 1004 that has a concave tail portion. The nose portion has a rounded bullet shape. A cannula 1006 extends through a longitudinal length of the spacer 1000. The spacer 1000 also has an opening 1008, which may hold various substances such as calcium triphosphate, bone marrow, or other injectable substances which improve the arthrodesis. The spacer 1000 is similar to spacer 700 but has a modified curvature of the tail portion, as is evident through comparison of FIG. 7 to FIG. 11 and comparison of FIG. 9 to FIG. 12. One or more exterior surfaces of the spacer 1000 may be textured. For example, one or more exterior surfaces may have teeth that serve to engage or "dig into" an endplate of the abutting vertebra.

Figure 14:
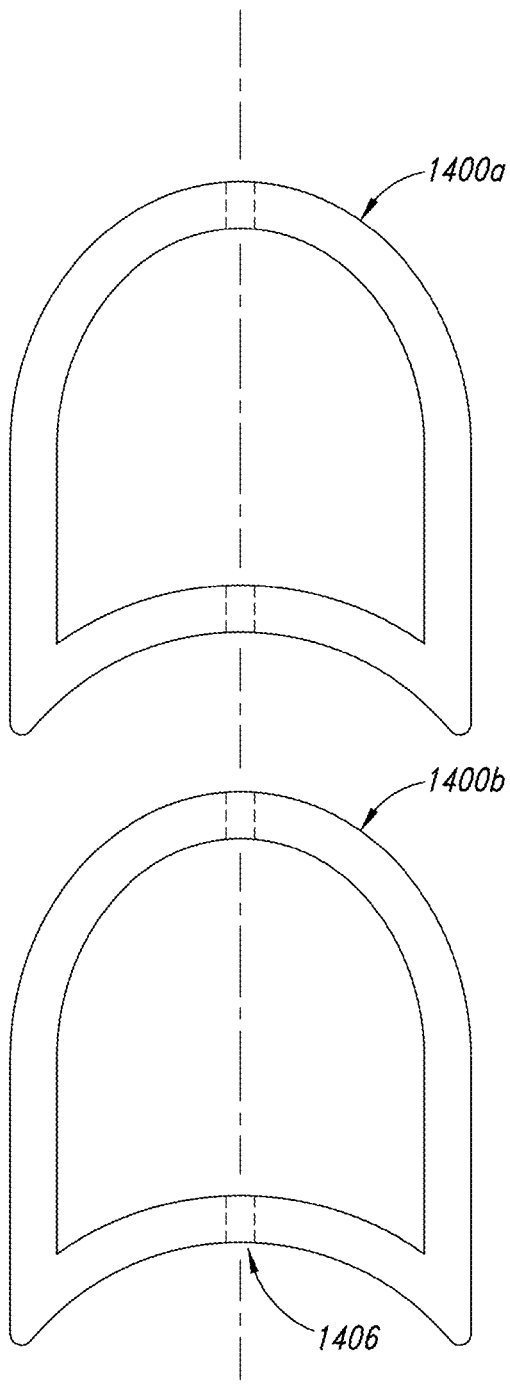
FIG. 14 is a plan view of two example intervertebral spacers, according to an example implementation of the present disclosure.
Figure 15:
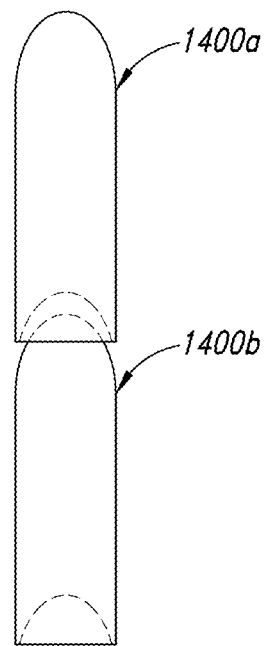
FIG. 15 is a side view of the two intervertebral spacers of FIG. 14 in a nested configuration, according to an example implementation of the present disclosure.

As yet another example, FIG. 14 is a plan view of two example intervertebral spacers 1400*a-b*, according to an example implementation of the present disclosure. FIG. 15 is a side view of the two intervertebral spacers 1400*a-b* of FIG. 14 in a nested relationship. A cannula 1406 extends through the two intervertebral spacers 1400*a-b* to permit insertion of a guide wire. The two intervertebral spacers 1400*a-b* are similar to spacers 700 and 1000 but have different dimensions, including a relatively larger central opening.

According to an aspect of the present disclosure, the various spacers provided herein may be sized differently in length, width, or height. For example, some spacers may have varying dimensions relative to other spacers. For example, some spacers may longer, wider, or taller than other spacers. As another example, some spacers may have asymmetric dimensions in one or more of the sagittal, coronal, or transverse planes. Thus, spacers having various different characteristics can be selected and combined into an assembly to match or correct a particular pathology presented by the subject.

Figure 13:
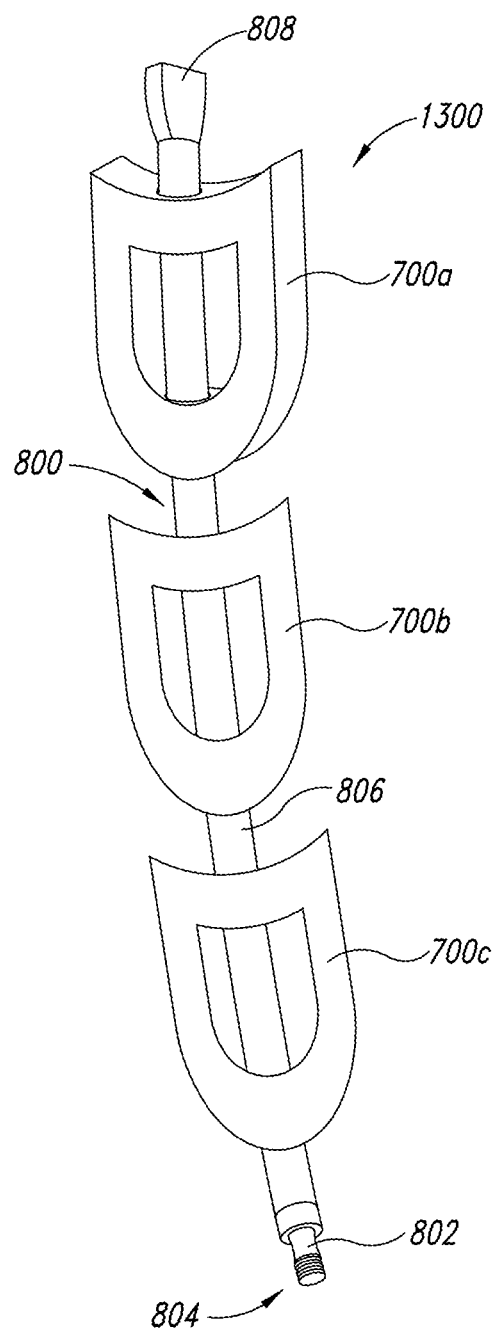
FIG. 13 is a perspective view of an example intervertebral spacer assembly, according to an example implementation of the present disclosure.

As one example, FIG. 13 is a perspective view of an example intervertebral spacer assembly 1300, according to an example implementation of the present disclosure. The assembly 1300 includes three spacers 700*a-c* coupled in series along the guide wire 800. In particular, the spacers 700*a-c* are respectively bullet shaped on the leading edge. They are also concaved in the trailing end. The leading end and the trailing end have equal and reciprocal dimensions, so that the trailing end of one spacer (e.g., 700*b*) fits snuggly on the leading end of another spacer (e.g., 700*a*). However, even when nested together, two adjacent spacers are articulable relative to each other, which enhances the insertability, flexibility, and intervertebral conformability of the implant.

One advantage of hinged or articulable spacers that interlock together is that the spacers can be modularly selected and combined to provide an individualized solution for each subject and disc space. The ability to select and modularly combine spacers of different dimensions provides an enormous number of permutations which enables the surgeon to individually accommodate various pathologies.

Referring again to FIG. 1C, after the trial spacers are selected at 134, then at 136 the selected trial spacers are inserted into the disc space to size for permanent implants. More particularly, once all the trial spacers are chosen and fitted together on an inserter, a stay wire is passed along the cannulated length of the spacers. The spacers are held together along the length of the wire during the insertion of the spacer assembly.

Figure 16:
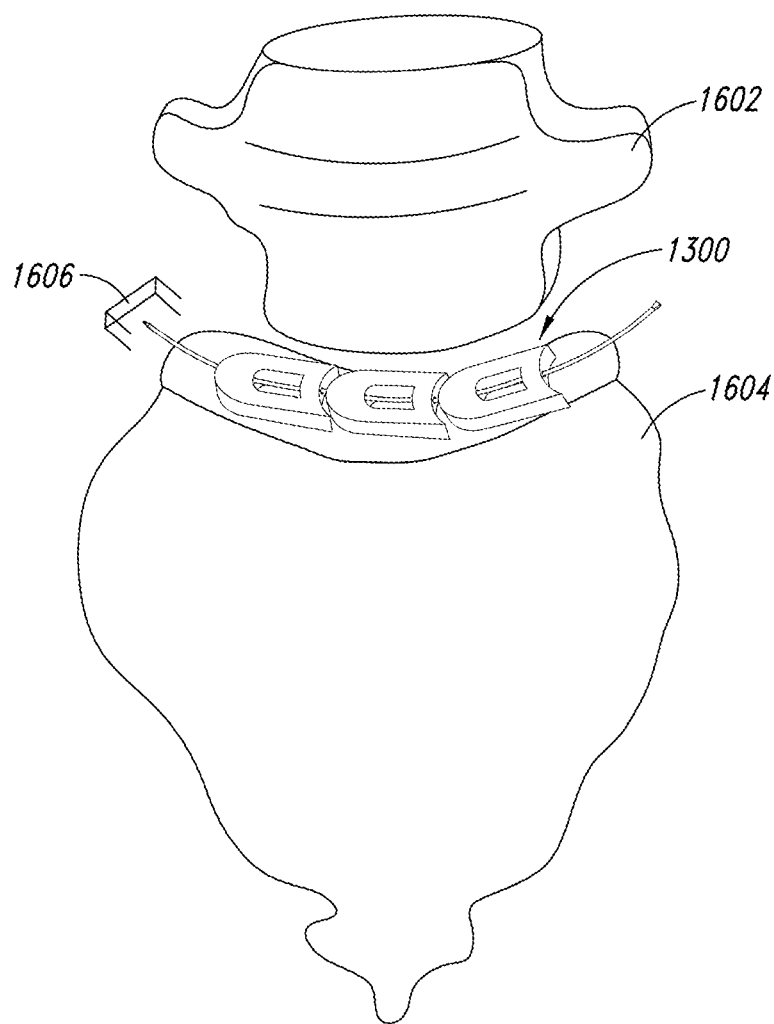
FIG. 16 is a simplified diagram of the intervertebral spacer assembly of FIG. 13 inserted in the disc space between the L5 and S1 vertebrae, according to an example implementation of the present disclosure.

As one example illustration, FIG. 16 is a simplified diagram of the intervertebral spacer assembly of FIG. 13 inserted in the disc space 1606 between the L5 vertebra 1602 and the S1 vertebra (shown generally as 1604), according to an example implementation of the present disclosure.

Referring again to FIG. 1C, at 138, the surgeon determines whether the inserted trial spacers are the correct size(s) to match the particular subject pathology. For example, fluoroscopy, endoscopy, or radioscopy may be used to determine the fit of the trial spacer assembly within the target disc space. Once the trialing period is completed, the trial spacers and wire are removed.

If the surgeon determines at 138 that the most recently selected trial spacers do not provide the correct fit to match or correct the particular subject pathology, then the surgeon may return to 134 and select a different set of trial spacers. The newly selected trial spacers will then be inserted again at 136 and the new fit will be analyzed at 138.

If the surgeon determines at 138 that the most recently selected trial spacers do provide the correct fit to match or correct the particular subject pathology, then at 140, the surgeon selects and assembles permanent spacers based on the correctly sized trial spacers.

Permanent intervertebral spacers are made of materials such as PEEK. As discussed above, they may be of varying size and length and angles. For example, the permanent spacers may be structured as shown in any of FIGS. 7-18. The permanent spacers are also cannulated along the length of the spacer, allowing a wire to pass along the length of multiple spacers, thus holding them together. The permanent spacers may be hollowed or solid.

At 142, the surgeon inserts the permanent spacer assembly into the patient and positions the permanent spacer assembly within the target disc space. Once all permanent spacers are in their final position, the wire and the inserter is removed.

At 144, the surgeon removes all instrumentation other than the permanent spacer assembly. At 146 the surgeon closes the surgical wound and finalizes the surgical procedure.

Figure 17:
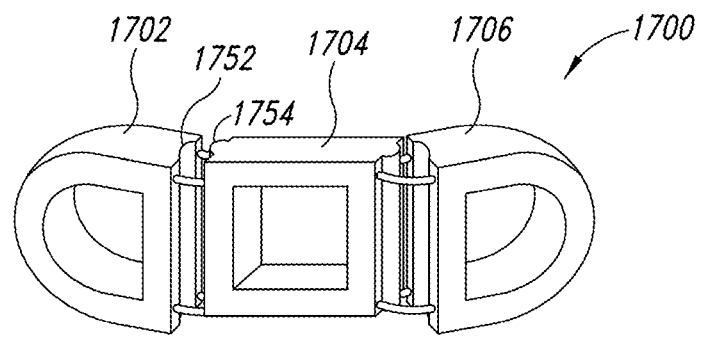
FIG. 17 is a perspective view of an example intervertebral spacer assembly, according to an example implementation of the present disclosure.

FIG. 17 is a perspective view of an example intervertebral spacer assembly 1700 according to an example implementation of the present disclosure.

The spacer assembly 1700 includes a leading spacer 1702, a middle spacer 1704, and a trailing spacer 1706. The leading spacer 1702 is articulatably coupled to the middle spacer 1704 and the middle spacer 1704 is articulatably coupled to the trailing spacer 1706. The leading spacer may have a first end and a second end opposite the first end; the middle spacer may have a third end and a fourth end opposite the third end; and the trailing spacer may have a fifth end and a sixth end opposite the fifth end. The second end and the third end may respectively have a first pair of complementary mating structures and the fourth end and the fifth end may respectively have a second pair of complementary mating structures. For example, as illustrated in FIG. 17, a first pair of complementary mating structures 1752 and 1754 enable the leading spacer 1702 and the middle spacer 1704 to nest together while remaining articulable.

The spacers 1702 and 1704 are coupled together by four retaining members. Likewise, spacers 1704 and 1706 are coupled together by four retaining members. In some implementations, the retaining members are resilient or elastic. In some implementations, the retaining members comprise one or more metal wires which traverses respective cannulas of the spacers 1702-1706.

Figure 18:
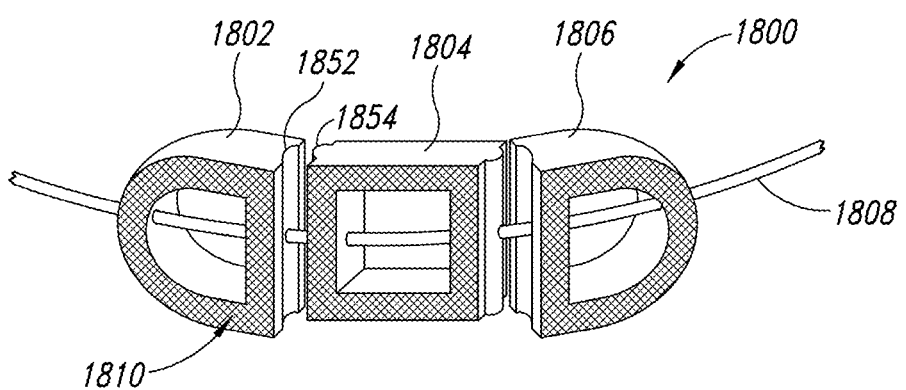
FIG. 18 is a perspective view of an example intervertebral spacer assembly, according to an example implementation of the present disclosure.

FIG. 18 is a perspective view of an example intervertebral spacer assembly 1800, according to an example implementation of the present disclosure.

The spacer assembly 1800 includes a leading spacer 1802, a middle spacer 1804, and a trailing spacer 1806. The leading spacer 1802 is articulatably coupled to the middle spacer 1804 and the middle spacer 1804 is articulatably coupled to the trailing spacer 1806. The leading spacer may have a first end and a second end opposite the first end; the middle spacer may have a third end and a fourth end opposite the third end; and the trailing spacer may have a fifth end and a sixth end opposite the fifth end. The second end and the third end may respectively have a first pair of complementary mating structures and the fourth end and the fifth end may respectively have a second pair of complementary mating structures. For example, as illustrated in FIG. 18, a first pair of complementary mating structures 1852 and 1854 enable the leading spacer 1802 and the middle spacer 1804 to nest together while remaining articulable.

The spacers 1802, 1804, and 1806 are coupled together in series by a single retaining member 1808. In some implementations, the retaining member is resilient or elastic. In some implementations, the retaining member is a guide wire that traverses respective cannulas of the spacers 1802-1806.

In some implementations, one or more exterior surfaces of any of spacers 1702-1706 and 1802-1806 may be textured or have other surface features such as teeth designed to grip the endplate of the abutting vertebra. For example, as illustrated in FIG. 18, the surface 1810 of spacer 1802 is shown as textured.

Those of skill in the art will recognize that many of the methods or algorithms set out herein may employ additional acts, may omit some acts, or may execute acts in a different order than specified.

The various implementations described above can be combined to provide further implementations. Aspects of the implementations can be modified, if necessary, to employ systems, circuits and concepts of the various patents, applications and publications to provide yet further implementations.

These and other changes can be made to the implementations in light of the above-detailed description. In general, in the following claims, the terms used should not be construed to limit the claims to the specific implementations disclosed in the specification and the claims, but should be construed to include all possible implementations along with the full scope of equivalents to which such claims are entitled. Accordingly, the claims are not limited by the disclosure.

What is claimed is:

1. An intervertebral spacer kit, comprising:
a plurality of candidate intervertebral spacers, each of the plurality of candidate intervertebral spacers releasably connectable to at least one other of the plurality of candidate intervertebral spacers, and wherein at least one of the plurality of candidate intervertebral spacers has different dimensions than others of the plurality of candidate intervertebral spacers; wherein each intervertebral spacer comprises a first end having a nose portion and an opposing second end having a tail portion, the nose portion sized and shaped to complementarily fit into the tail portion of an adjacent intervertebral spacer; and wherein each intervertebral spacer of the plurality of intervertebral spacers comprises a respective cannula extending through the intervertebral spacer, the cannula of each intervertebral spacer sized and shaped to receive a wire that extends through the cannula of each of the plurality of intervertebral spacers.

2. The intervertebral spacer kit of claim 1 wherein the plurality of candidate intervertebral spacers include a plurality of modular candidate intervertebral spacers, each modular candidate intervertebral spacer having a first end and a second end, the first end sized and shaped to nest with the second end of an adjacent modular candidate intervertebral spacer to form an articulable joint.

3. The intervertebral spacer kit of claim 1 wherein at least one of the plurality of candidate intervertebral spacers has asymmetric coronal dimensions.

4. The intervertebral spacer kit of claim 1 wherein at least one of the plurality of candidate intervertebral spacers has asymmetric sagittal dimensions.

5. An intervertebral spacer assembly, comprising:
a plurality of articulated intervertebral spacers coupled in series, each intervertebral spacer releasably connectable to an adjacent intervertebral spacer, wherein each intervertebral spacer comprises a first end having a nose portion and an opposing second end having a tail portion, the nose portion sized and shaped to complementarily fit into the tail portion of an adjacent intervertebral spacer; and wherein each intervertebral spacer of the plurality of intervertebral spacers comprises a respective cannula extending through the intervertebral spacer, the cannula of each intervertebral spacer sized and shaped to receive a wire that extends through the cannula of each of the plurality of intervertebral spacers.

6. The intervertebral spacer assembly of claim 5 wherein the plurality of intervertebral spacers are selected from a plurality of candidate intervertebral spacers, wherein at least one of the plurality of candidate intervertebral spacers has different dimensions than remaining candidate intervertebral spacers.

7. The intervertebral spacer assembly of claim 5 wherein the nose portion has a rounded bullet-shape and the tail portion a concave shape sized and shaped to receive the nose portion of at least one other intervertebral spacer of the plurality of intervertebral spacers.

8. The intervertebral spacer assembly of claim 5 wherein each intervertebral spacer comprises a cannula extending from a first exterior surface of the tail portion through the nose portion to reach a second exterior surface of the nose portion.

9. The intervertebral spacer assembly of claim 5 wherein the plurality of intervertebral spacers comprises a leading spacer, a middle spacer, and a trailing spacer.

10. The intervertebral spacer assembly of claim 9 wherein the leading spacer is articulatably coupled to the middle spacer and the middle spacer is articulatably coupled to the trailing spacer.

11. The intervertebral spacer assembly of claim 9 wherein the leading spacer comprises a first end and a second end opposite the first end, the middle spacer comprises a third end and a fourth end opposite the third end, the trailing spacer comprises a fifth end and a sixth end opposite the fifth end, the second end and the third end respectively have a first pair of complementary mating structures, and the fourth end and the fifth end respectively have a second pair of complementary mating structures.

* * * * *